(12) United States Patent
Su et al.

(10) Patent No.: US 9,839,354 B2
(45) Date of Patent: Dec. 12, 2017

(54) EMERGENCY CALL APPARATUS, EMERGENCY CALL SYSTEM AND BACKUP METHOD THEREOF

(71) Applicant: MELTEN corporation, New Taipei (TW)

(72) Inventors: Shih-Hsien Su, New Taipei (TW); Han-Wu Liu, New Taipei (TW)

(73) Assignee: MELTEN corporation, Taipei (TW)

( * ) Notice: Subject to any disclaimer, the term of this patent is extended or adjusted under 35 U.S.C. 154(b) by 54 days.

(21) Appl. No.: 15/050,469

(22) Filed: Feb. 23, 2016

(65) Prior Publication Data
US 2017/0238801 A1 Aug. 24, 2017

(51) Int. Cl.
| | |
|---|---|
| G08B 29/00 | (2006.01) |
| A61B 5/00 | (2006.01) |
| H04L 29/08 | (2006.01) |
| A61B 5/0205 | (2006.01) |
| A61B 5/11 | (2006.01) |

(52) U.S. Cl.
CPC ............ *A61B 5/0015* (2013.01); *A61B 5/747* (2013.01); *H04L 67/1095* (2013.01); *A61B 5/0205* (2013.01); *A61B 5/1115* (2013.01)

(58) Field of Classification Search
CPC .......................... A61B 5/0015; H04L 67/1095
USPC ....................................................... 340/507
See application file for complete search history.

(56) References Cited

U.S. PATENT DOCUMENTS

| | | | | |
|---|---|---|---|---|
| 4,104,710 A | * | 8/1978 | Damico | A47B 79/00 174/501 |
| 4,821,470 A | * | 4/1989 | Kappers | A61G 12/005 174/480 |
| 5,060,425 A | * | 10/1991 | Kappers | H02G 3/0431 312/297 |
| 7,319,386 B2 | * | 1/2008 | Collins, Jr. | A61B 5/1115 340/286.07 |
| 7,425,679 B2 | * | 9/2008 | Kasten | A61G 12/002 174/480 |
| 8,401,874 B2 | * | 3/2013 | Rosenfeld | A61B 5/411 600/300 |
| 8,456,286 B2 | * | 6/2013 | Schuman | G08B 5/222 340/286.07 |
| 8,640,391 B2 | * | 2/2014 | Newkirk | E04F 19/08 52/220.1 |

(Continued)

Primary Examiner — Eric M Blount
(74) Attorney, Agent, or Firm — JCIPRNET

(57) ABSTRACT

An emergency call apparatus, an emergency call system and a backup method thereof are provided. The emergency call system includes a bedside station, a managing server and at least one target device. In the method, the bedside station detects a triggering signal of an emergency call and then detects a network connection with the managing server. In response to detecting the network connection is connected, the bedside station transmits a request of the emergency call to the managing server and establishes an emergency call connection with the at least one target device according to connection information of the at least one target device stored in the managing server. In response to detecting the network connection is disconnected, the bedside station establishes the emergency call connection with the target device according to a backup of the connection information of the target device stored in the bedside station.

10 Claims, 4 Drawing Sheets

(56) References Cited

U.S. PATENT DOCUMENTS

| | | | | |
|---|---|---|---|---|
| 2003/0009952 A1* | 1/2003 | Gallant | ................... | A61G 7/00 |
| | | | | 52/36.4 |
| 2008/0018435 A1* | 1/2008 | Brown | ................ | G06F 19/3418 |
| | | | | 340/286.07 |
| 2011/0209835 A1* | 9/2011 | Balbona | ............... | A61G 12/005 |
| | | | | 160/127 |

* cited by examiner

EMERGENCY CALL APPARATUS, EMERGENCY CALL SYSTEM AND BACKUP METHOD THEREOF

BACKGROUND OF THE DISCLOSURE

Field of the Disclosure

The disclosure relates to a method and a system for healthcare communication, and particularly relates to an emergency call apparatus, an emergency call system and a backup method thereof.

Description of Related Art

A variety of patient monitoring devices are commonly employed in hospitals for monitoring physiological condition of patients and recording medical data such as heart rate, blood pressure, blood glucose and electrocardiogram. Those devices act in a stand-alone manner that provide alarms when detecting an abnormal condition of the patient.

The conventional nurse call system is established through network and operated by a managing server. In case that the server is down or the network connection is unstable or disconnected, the nurse call system may suffer from malfunction, which places patients at risk of failing to call for help.

SUMMARY OF THE DISCLOSURE

The disclosure is directed to an emergency call apparatus, an emergency call system and a backup method thereof, through which an emergency call made by the emergency call apparatus can be transmitted to the corresponding target devices by the emergency call apparatus itself according to a backup of the connection information of the target devices such that a more reliable emergency call system is achieved.

The disclosure provides an emergency call apparatus which comprises a bedside station. The bedside station is disposed on a panel of a gas supply system, and configured to be powered by one of a network cable and a power source of the gas supply system and make at least one target device present an emergency call, wherein the gas supply system is mounted on a wall alongside a hospital bed for supplying medical gases.

In an embodiment of the disclosure, the bedside station comprises a network connecting device, a storage device, and a processor. The network connecting device is configured to connect a network. The storage device is configured to store connection information of the at least one target device. The processor is configured to establish an emergency call connection for presenting the emergency call with the at least one target device through the network according to the connection information.

In an embodiment of the disclosure, the bedside station further comprises at least one interface device, which is configured to connect with at least one patient monitoring device and receive patient related data detected by the at least one patient monitoring device, wherein the processor is configured to transmit the patient related data to the at least one target device through the network.

In an embodiment of the disclosure, the storage device is configured to store the patient related data.

The disclosure provides an emergency call system which includes at least one target device and a bedside station. The at least one target device is respectively configured to present an emergency call. The bedside station is disposed on a panel of a gas supply system, and configured to be powered by one of a network cable and a power source of the gas supply system and establish an emergency call connection for presenting the emergency call with the at least one target device, wherein the gas supply system is mounted on a wall alongside a hospital bed for supplying medical gases.

In an embodiment of the disclosure, the system further includes a managing server, which is configured to store connection information of the at least one target device.

In an embodiment of the disclosure, the bedside station is configured to backup the connection information of the at least one target device stored in the managing server, in which the connection information comprises a phone number, an internet protocol address, an email address, a uniform resource locator, or a service set identifier.

In an embodiment of the disclosure, the bedside station is configured to detect a network connection with the managing server and establish the emergency call connection with the at least one target device according to a backup of the connection information of the at least one target device stored in the bedside station in response to detecting the network connection is disconnected.

In an embodiment of the disclosure, the bedside station is configured to detect a network connection with the managing server, receive patient related data from at least one patient monitoring device, store the patient related data in response to detecting the network connection is disconnected, and upload the patient related data to the managing server in response to detecting the network connection is recovered.

The disclosure provides a backup method of an emergency call system, wherein the emergency call system includes a bedside station, a managing server and at least one target device. In the method, the bedside station detects a triggering signal of an emergency call and then detects a network connection with the managing server. In response to detecting the network connection is connected, the bedside station transmits a request of the emergency call to the managing server and establishes an emergency call connection with the at least one target device according to connection information of the at least one target device stored in the managing server. In response to detecting the network connection is disconnected, the bedside station establishes the emergency call connection with the at least one target device according to a backup of the connection information of the at least one target device stored in the bedside station.

In an embodiment of the disclosure, the method further backs up the connection information of the at least one target device stored in the managing server periodically by the bedside station.

In an embodiment of the disclosure, the method further receives patient related data from at least one patient monitoring device and uploads the patient related data to the managing server.

In an embodiment of the disclosure, in response to detecting the network connection is disconnected, the method further receives patient related data from at least one patient monitoring device by the bedside station, stores the patient related data in a storage device of the bedside station in response to detecting the network connection is disconnected, and uploads the patient related data to the managing server by the bedside station in response to detecting the network connection is connected.

In an embodiment of the disclosure, the at least one target device comprises a pager, a watch, a phone, a tablet, a computer, a corridor indicator, a number calling machine, a medical cart, or a hospital bed.

In an embodiment of the disclosure, the connection information comprises a phone number, an internet protocol address, an email address, a uniform resource locator, or a service set identifier.

Based on the above, in the emergency call apparatus, the emergency call system and the backup method thereof of the present disclosure, the connection information of the target devices for establishing emergency call connections is backed up in the bedside station from a managing server. Accordingly, in response to detecting the network connection with the managing server is disconnected, the bedside station can establish the emergency call connection with the target devices without the managing server. Therefore, a more reliable emergency call system is achieved.

In order to make the aforementioned and other features and advantages of the disclosure comprehensible, several exemplary embodiments accompanied with figures are described in detail below.

BRIEF DESCRIPTION OF THE DRAWINGS

The accompanying drawings are included to provide a further understanding of the disclosure, and are incorporated in and constitute a part of this specification. The drawings illustrate embodiments of the disclosure and, together with the description, serve to explain the principles of the disclosure.

DESCRIPTION OF EMBODIMENTS

In the disclosure, a bedside station configured for an emergency call is disposed on a panel of a gas supply system and powered by a network cable or a power source of the gas supply system mounted on a wall alongside a hospital bed. The bedside station is further configured to backup a managing server of an emergency call system and is capable of establishing an emergency call connection for presenting the emergency call with target devices such as a phone or a computer at a nurse console, a medical cart or a caregiver's pager, watch, tablet, or phone. In case that the managing server is down or the network connection with the managing server is unstable or disconnected, the bedside station can still provide functions such as emergency calls on the target devices and temporal storage of patient related data. As a result, a more reliable emergency call system is achieved.

Figure 1:
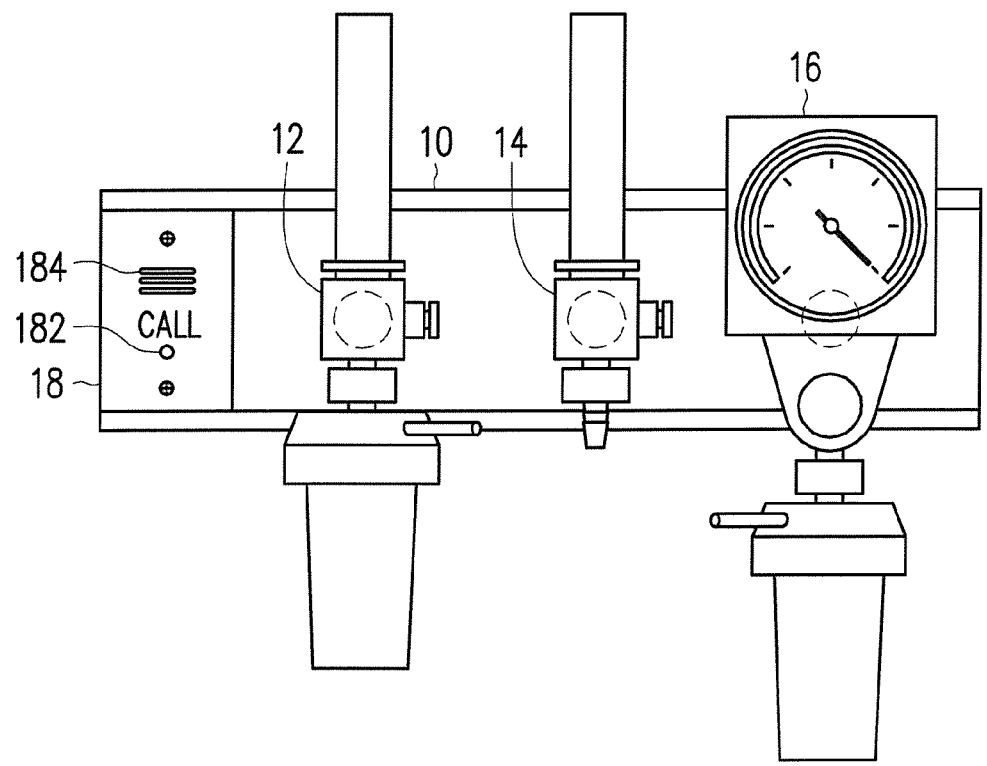
FIG. 1 is a schematic diagram of an emergency call apparatus according to an embodiment of the disclosure.

FIG. 1 is a schematic diagram of an emergency call apparatus according to an embodiment of the disclosure. Referring to FIG. 1, a gas supply system is mounted on a wall alongside a hospital bed and comprises a panel 10, a power source, and gas valves for supplying medical gases, such as an oxygen valve 12 for supplying oxygen, a compressed air valve 14 for supplying air, and a nitrous oxide valve 16 for supplying nitrous oxide. An emergency call apparatus 18 is configured as a bedside station, which is disposed on the panel 10 of the gas supply system and powered by a network cable or the power source of the gas supply system for omitting an external power cord. The bedside station 18 comprises a physical button 182 for a patient to make a nurse call and a conversation interface 184 for the patient to talk with a caregiver.

Specifically, the bedside station 18 may further include a gateway for transferring patient related data detected by patient monitoring devices, such as a bed occupancy sensor or a bed-leaving sensor, a heart rate monitor, a body thermometer, a blood pressure meter, a blood glucose meter, a blood oxygen monitor, an electrocardiogram (ECG/EKG) monitor or a photoplethysmography (PPG) monitor, to a managing server of an emergency call system or other target devices such as a pager, a watch, a phone, a tablet, a computer, a corridor indicator, a number calling machine, a caption machine, a medical cart, or a hospital bed, which are not limited by the disclosure.

Figure 2:
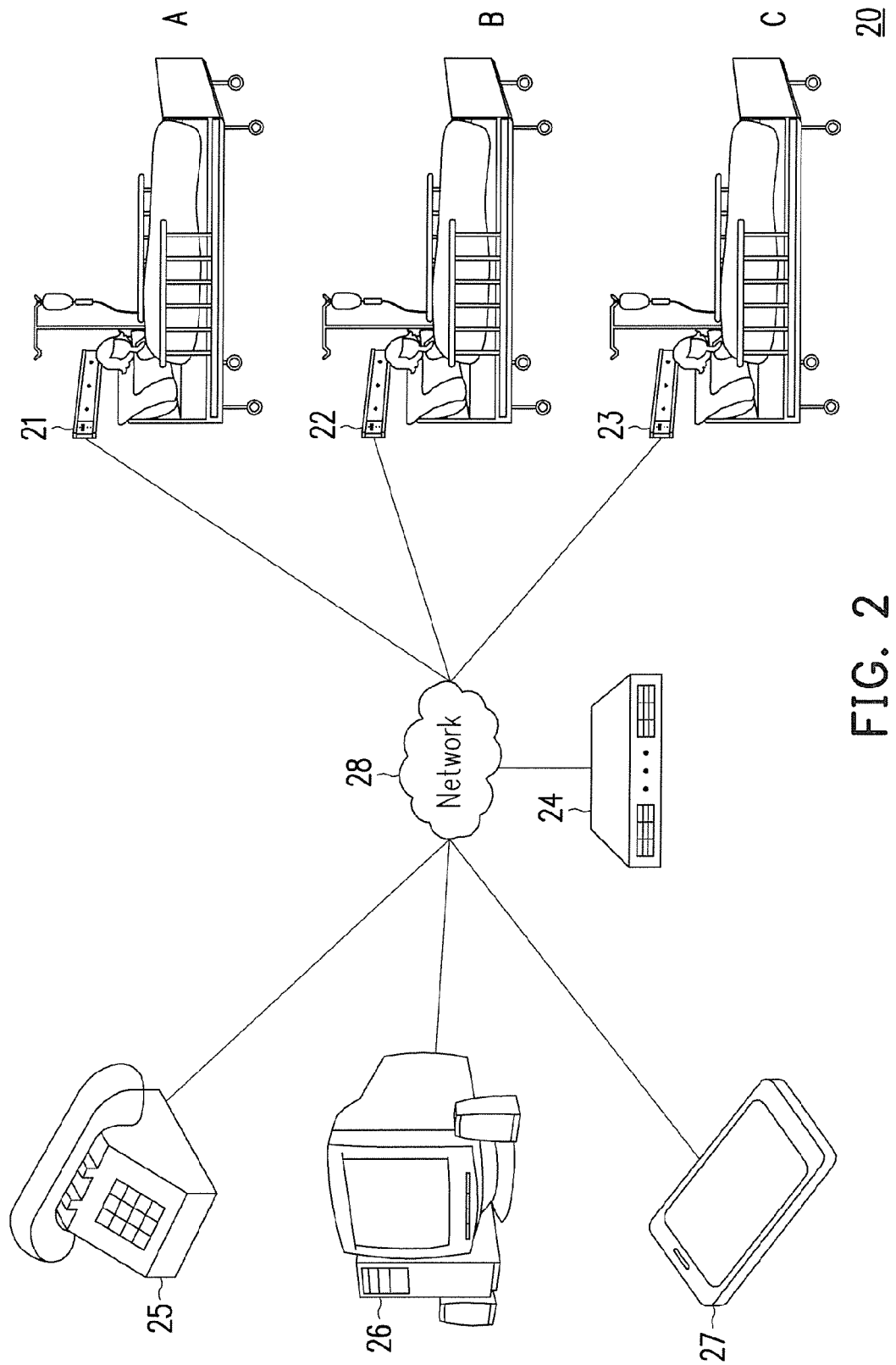
FIG. 2 is a schematic diagram of an emergency call system according to an embodiment of the disclosure.

In detail, FIG. 2 is a schematic diagram of an emergency call system according to an embodiment of the disclosure. Referring to FIG. 2, an emergency call system 20 of the present embodiment comprises at least one emergency call apparatus (e.g. bedside station 21, 22 or 23), a managing server 24 and at least one target device (e.g. a telephone 25 and a computer 26 at a nurse console and a mobile phone 27 of a nurse who takes care of the patients A, B and C). The mange server 24 respectively connects the bedside stations 21 to 23 through a network 28 and stores connection information of the target devices. It is noted that the aforesaid network 28 comprises Ethernet, Intranet or Internet, which is not limited by the disclosure. For example, the mange server 24 may connect with the bedside stations 21, 22 and 23 through Ethernet.

The managing server 24 records the connection information of those target devices such that when receiving a request of an emergency call from the bedside station 21, 22 or 23 of which the physical button 182 is pressed or where any of the patient related data is abnormal, the managing server 24 is able to return the connection information of the right target devices, necessary to present the emergency call, to the bedside station of which the physical button 182 is pressed or where any of the patient related data is abnormal. The bedside station will establish emergency call connections with the right target devices to make them present the emergency call through the network 28 according to the connection information returned.

Through the assistance of the managing server 24, an emergency call triggered by the bedside station 21, 22 or 23 can be transmitted to the right, corresponding target devices (e.g. the telephone 25, the computer 26 and/or the mobile phone 27) such that the patient A, B or C may timely find an appropriate caregiver and get help from the caregiver.

In addition to voice calls, the bedside stations 21, 22 and 23 also respectively receive patient related data from the patient monitoring devices configured for the patients A, B and C and transmit, through the assistance of the managing server 24, the patient related data to the right, corresponding target devices so as to assist the caregiver in judging current condition of the patients A, B and C. The patient related data transmitted by the bedside stations 21, 22 and 23 may further be stored in a database of the managing server 24 for subsequent tracing.

It is noted that, in the present disclosure, the bedside stations 21, 22 and 23 respectively backup periodically the connection information of the target devices from the managing server 24 such that the bed stations 21, 22 and 23 are able to each establish the emergency call connections with the target devices according to the backup of the connection information of the target devices stored in the bedside stations 21, 22 and 23 in case the managing server 24 is down or the network connection between the managing server 24 and the bed station 21, 22 and 23 is unstable or disconnected. The connection information comprises a phone number, an internet protocol (IP) address, an email address, a uniform resource locator (URL), a service set identifier (SSID), or any other information required for connecting with the target devices, which is not limited by the disclosure.

Figure 3:
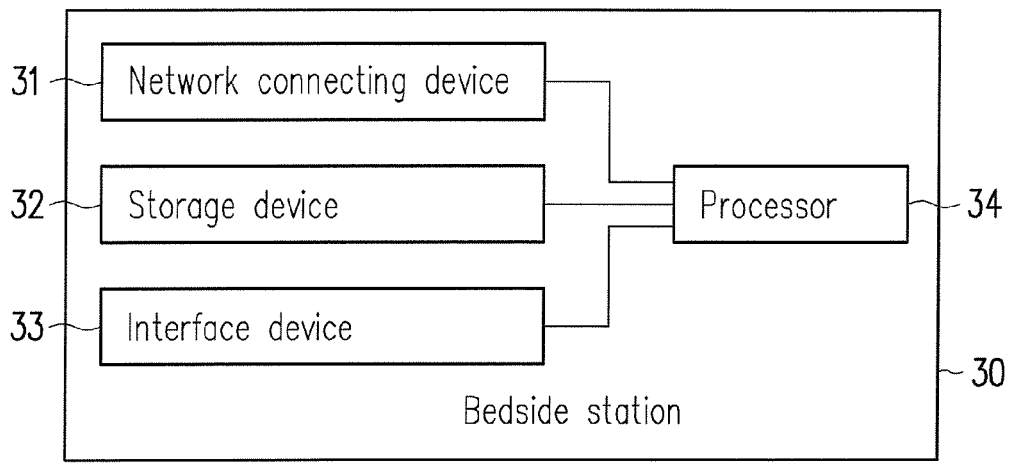
FIG. 3 is a block diagram of a bedside station according to an embodiment of the disclosure.

FIG. 3 is a block diagram of a bedside station according to an embodiment of the disclosure. Referring to FIG. 3, the bedside station 30 is, for example, configured as the emergency call apparatus 18 shown in FIG. 1. That is, the bedside station 30 is disposed on a panel of a gas supply system and powered by one of a network cable and a power source of the gas supply system mounted on a wall alongside a hospital bed. The bedside station 30 comprises a network connecting device 31, a storage device 32, at least one interface device 33 and a processor 34, and functions thereof are respectively described below.

The network connecting device 31 is, for example, a network card or any other network equipment that supports Ethernet or wireless network standards such as 802.11g, 802.11n, or 802.11ac. The network connecting device 31 may use transmission control protocol/internet protocol (TCP/IP), user datagram protocol (UDP) or other high-level communication protocols to connect with the network and transmit data through the network.

The storage device 32 is, for example, a fixed or a movable device in any possible forms including a random access memory (RAM), a read-only memory (ROM), a flash memory or any other similar device, or a combination of the above-mentioned devices. In one embodiment, the storage device 32 is configured to store the connection information of the target devices that correspond to the bedside station 30. In another embodiment, the storage device 32 is further configured to store the patient related data received from the patient monitoring devices connected with the bedside station 30.

The interface device 33 is, for example, a universal serial bus (USB) device, a RS232 device, an internal bi-directional communication (I2C) device, a universal asynchronous receiver-transmitter (UART) device, a Bluetooth device, or any other input/output (I/O) device, or a combination of the above-mentioned devices, which is not limited by the disclosure. The interface device 33 is configured to connect with the patient monitoring devices so as to receive patient related data detected by the patient monitoring devices.

The processor 34 is, for example, a central processing unit (CPU), or a programmable general purpose or special purpose microprocessor, a digital signal processor (DSP), a programmable controller, an application specific integrated circuit (ASIC) or any other similar device or a combination of the above devices. In the present disclosure, the processor 34 is coupled to the network connecting device 31, the storage device 32 and the interface device 33 so as to execute the backup method of an emergency call system of the disclosure.

Figure 4:
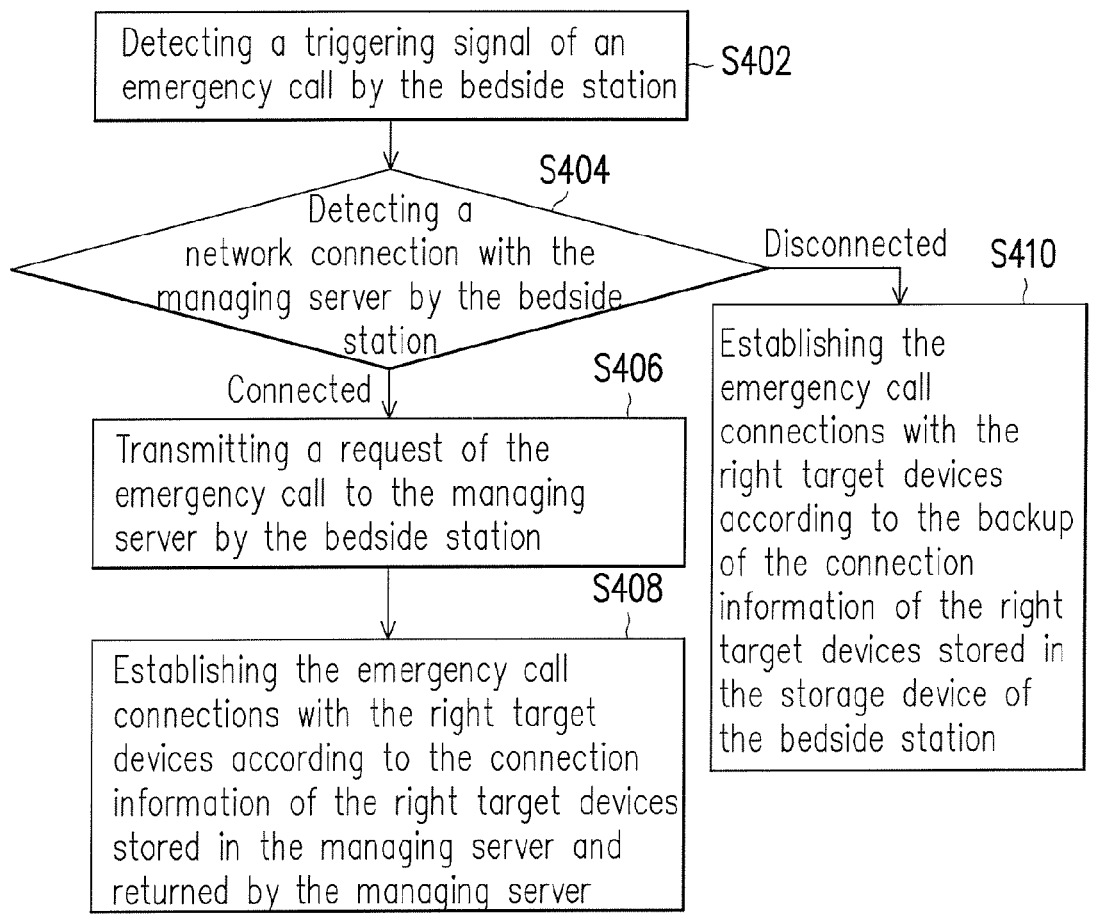
FIG. 4 is a flow chart illustrating a backup method of an emergency call system according to an embodiment of the disclosure.

In detail, FIG. 4 is a flow chart illustrating a backup method of an emergency call system according to an embodiment of the disclosure. Referring to FIG. 3 and FIG. 4, the method of the present example is applicable to the bedside station 30 in FIG. 3. In the following, the method of the present embodiment is described in detail with reference to the elements of the bedside station 30 in FIG. 3.

First, the bedside station 30 detects a triggering signal of an emergency call by using the interface device 33 (step S402). In one embodiment, the interface device 33 may connect with a physical button disposed on the bedside station 30 for the patient to trigger the emergency call. In another embodiment, the interface device 33 may connect with a pillow speaker/microphone which is placed nearby the pillow of the patient for the patient to trigger the emergency call. In another embodiment, the interface device 33 may receive patient related data detected by the patient monitoring devices. The processor 34 judges if any of the patient related data is abnormal, for example, above a high value or below a low value, for the patient to trigger the emergency call.

Then, the bedside station 30 detects a network connection with a managing server (not shown) by using the network connecting device 31 (step S404). In one embodiment, the network connecting device 31 may transmit a data packet by using TCP/IP to the managing server so as to detect the network connection with the managing server according to a returned data packet. In another embodiment, the network connecting device 31 may use packet internet groper (PING) to detect the network connection with the managing server, which is not limited by the disclosure.

In response to detecting the network connection is connected, the bedside station 30 transmits a request of the emergency call to the managing server by using the network connecting device 31 (step S406). According to the request of the emergency call, the managing server returns the connection information of the right target devices, necessary to present the emergency call, to the bedside station 30. The bedside station 30 establishes emergency call connections with the right target devices according to the connection information of the right target devices stored in the managing server and returned by the managing server (step S408).

The bedside station 30 further backups periodically in the storage device 32 the connection information of the target devices stored in the managing server.

In response to detecting the network connection is disconnected, the bedside station 30 establishes the emergency call connections with the right, corresponding target devices by using the network connecting device 31 according to the backup of the connection information of the target devices stored in the storage device 32 of the bedside station 30 (step S410).

Based on the above, the bedside station 30 can establish the emergency call connections with the corresponding target devices by itself to make the corresponding target devices present the emergency call without the managing server, and therefore a more reliable emergency call system is achieved.

The bedside station 30 further supports the backup of patient related data of patient. An embodiment is given below for further illustration.

Figure 5:
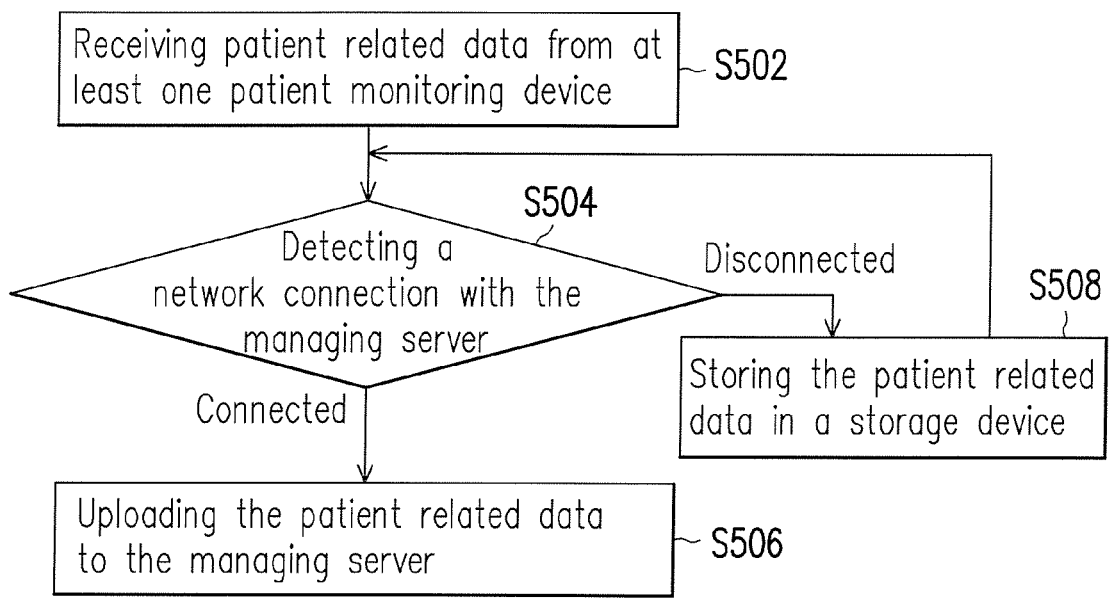
FIG. 5 is a flow chart illustrating a backup method of an emergency call system according to an embodiment of the disclosure.

FIG. 5 is a flow chart illustrating a backup method of an emergency call system according to an embodiment of the disclosure. Referring to FIG. 3 and FIG. 5, the method of the present example is applicable to the bedside station 30 in FIG. 3. In the following, the method of the present embodiment is described in detail with reference to the elements of the bedside station 30 in FIG. 3.

First, the bedside station 30 receives patient related data from at least one patient monitoring device by using the interface device 33 (step S502). The patient related data comprises bed occupied time, bed-leaving time, heart rate, body temperature, blood pressure, blood glucose, electrocardiogram or any other physiological data of the patient, and may further comprise other related information such as a bed condition and a room status, which is not limited by the disclosure.

Then, the bedside station 30 detects a network connection with a managing server (not shown) by using the network connecting device 31 (step S504). The step S504 is identical or similar to the step S404 in the foregoing embodiment, and therefore the detail is not repeated herein.

In response to detecting the network connection is connected, the bedside station 30 uploads the patient related data to the managing server by using the network connecting device 31 (step S506), and in response to detecting the network connection is disconnected, the bedside station 30 stores the patient related data in the storage device 32 (step S508).

It is noted that, in case the network connection is determined as disconnected, the bedside station 30 may keep trying to recover the network connection with the managing server at a predetermined time interval by using the network connecting device 31, and once the network connection is recovered, the bedside station 30 uploads the patient related data temporally stored in the storage device 32 to the managing server.

Based on the above, the bedside station 30 can temporally store the patient related data of the patient and timely uploads the patient related data to the managing server so as to keep integrity of the patient related data of the patient.

In summary, in the emergency call apparatus, the emergency call system and the backup method thereof of the present disclosure, each of the emergency call apparatuses disposed alongside the hospital bed backs up the connection information of the target devices from the managing server. Accordingly, even though the managing server is disconnected with the emergency call apparatus due to any reason, the emergency call apparatus can still establish the emergency call connections with the corresponding target devices to make the corresponding target devices present the emergency call and provide required patient related data for the corresponding target devices by itself. Therefore, a more reliable emergency call system is achieved.

It will be apparent to those skilled in the art that various modifications and variations can be made to the structure of the disclosure without departing from the scope or spirit of the disclosure. In view of the foregoing, it is intended that the disclosure cover modifications and variations of this disclosure provided they fall within the scope of the following claims and their equivalents.

What is claimed is:

1. An emergency call system, comprising:
   at least one target device, respectively configured to present an emergency call;
   a bedside station, disposed on a panel of a gas supply system, and configured to be powered by one of a network cable and a power source of the gas supply system and establish an emergency call connection for presenting the emergency call with the at least one target device, wherein the gas supply system is mounted on a wall alongside a hospital bed for supplying medical gases; and
   a managing server, configured to store connection information of the at least one target device,
   wherein the bedside station is configured to backup the connection information of the at least one target device stored in the managing server.

2. The apparatus as claimed in claim 1, wherein the connection information comprises a phone number, an internet protocol address, an email address, a uniform resource locator, or a service set identifier.

3. The system as claimed in claim 1, wherein the bedside station is configured to detect a network connection with the managing server and establish the emergency call connection with the at least one target device according to a backup of the connection information of the at least one target device stored in the bedside station in response to detecting the network connection is disconnected.

4. The system as claimed in claim 1, wherein the bedside station is configured to detect a network connection with the managing server, receive patient related data from at least one patient monitoring device, store the patient related data in response to detecting the network connection is disconnected, and upload the patient related data to the managing server in response to detecting the network connection is recovered.

5. The system as claimed in claim 1, wherein the at least one target device comprises a pager, a watch, a phone, a tablet, a computer, a corridor indicator, a number calling machine, a caption machine, a medical cart, or a hospital bed.

6. A backup method of an emergency call system, wherein the emergency call system comprises a bedside station, a managing server and at least one target device, the method comprising:
   detecting a triggering signal of an emergency call by the bedside station;
   detecting a network connection with the managing server by the bedside station;
   in response to detecting the network connection is connected, transmitting a request of the emergency call to the managing server by the bedside station and establishing an emergency call connection with the at least one target device by the bedside station according to connection information of the at least one target device stored in the managing server; and
   in response to detecting the network connection is disconnected, establishing the emergency call connection with the at least one target device by the bedside station according to a backup of the connection information of the at least one target device stored in the bedside station.

7. The method as claimed in claim 6, further comprising:
   backuping the connection information of the at least one target device stored in the managing server periodically by the bedside station.

8. The method as claimed in claim 6, further comprising:
   receiving patient related data from at least one patient monitoring device by the bedside station;
   storing the patient related data in a storage device of the bedside station in response to detecting the network connection is disconnected; and
   uploading the patient related data to the managing server by the bedside station in response to detecting the network connection is connected.

9. The method as claimed in claim 6, wherein the at least one target device comprises a pager, a watch, a phone, a tablet, a computer, a corridor indicator, a number calling machine, a caption machine, a medical cart, or a hospital bed.

10. The method as claimed in claim 6, wherein the connection information comprises a phone number, an internet protocol address, an email address, a uniform resource locator, or a service set identifier.

* * * * *